(12) United States Patent
Edmonds

(10) Patent No.: US 6,303,925 B1
(45) Date of Patent: Oct. 16, 2001

(54) APPARATUS AND METHOD FOR DISTINGUISHING PAPER ARTICLES FROM PLASTIC ARTICLES

(76) Inventor: Patricia Alaine Edmonds, 2316 Lawnwood Cir., Baltimore, MD (US) 21207

(*) Notice: Subject to any disclaimer, the term of this patent is extended or adjusted under 35 U.S.C. 154(b) by 0 days.

(21) Appl. No.: 09/256,318

(22) Filed: Feb. 24, 1999

(51) Int. Cl.[7] .................. G01N 9/04; G01N 21/00
(52) U.S. Cl. .................. 250/223 R; 356/239.1; 356/432
(58) Field of Search .................. 250/340, 341.1, 250/341.6, 330, 339.08, 223 R; 356/435, 239.1, 238.3, 438

(56) References Cited

U.S. PATENT DOCUMENTS

| | | |
|---|---|---|
| 3,216,568 | 11/1965 | Jacob et al. . |
| 3,747,755 | 7/1973 | Senturia et al. . |
| 3,781,531 | 12/1973 | Baker . |
| 3,975,261 * | 8/1976 | Beck .................. 250/555 |
| 3,980,180 * | 9/1976 | Jamieson .................. 356/201 |
| 5,141,110 | 8/1992 | Trischan et al. . |
| 5,365,075 * | 11/1994 | Peterson .................. 356/239 |
| 5,405,014 | 4/1995 | Krieg et al. . |
| 5,423,431 * | 6/1995 | Westin .................. 209/539 |
| 5,435,445 | 7/1995 | Dellinger, Jr. et al. . |
| 5,465,822 | 11/1995 | Dewoolfson et al. . |
| 5,489,778 * | 2/1996 | Burmester et al. .................. 250/341.6 |
| 5,518,124 | 5/1996 | Sommer, Jr. et al. . |
| 5,590,791 | 1/1997 | Gschweitl . |
| 5,632,381 * | 5/1997 | Thust et al. .................. 209/44.1 |

OTHER PUBLICATIONS

Jenkins, Francis A.; White, Harvey E.; Fundamentals of Optics, McGraw–Hill Book Company, 1976, 4th edition, p. 457.*

* cited by examiner

Primary Examiner—Frank G. Font
Assistant Examiner—Roy M. Punnoose
(74) Attorney, Agent, or Firm—Bacon & Thomas

(57) ABSTRACT

An apparatus and method for distinguishing paper from plastic articles involves a coherent light source such as a laser, a device for conveying paper and plastic objects through the path of the laser, and a detector arranged to detect light passing through the objects and to measure the intensity of the light, connected to a controller that includes an analog thresholding circuit, computer, or digital logic circuit. The controller determines whether a passing object is a paper object or a plastic object based either on whether the measure light intensity is below or above a threshold as the object passes between the light source and the detector, or on whether the light intensity increases or decreases as the object is moved towards or away from the detector. The detector must be a minimum distance from the detector that is determined by the points at which the intensity of light transmitted through a paper object decreases and the intensity of light transmitted through a plastic object increases.

9 Claims, 2 Drawing Sheets

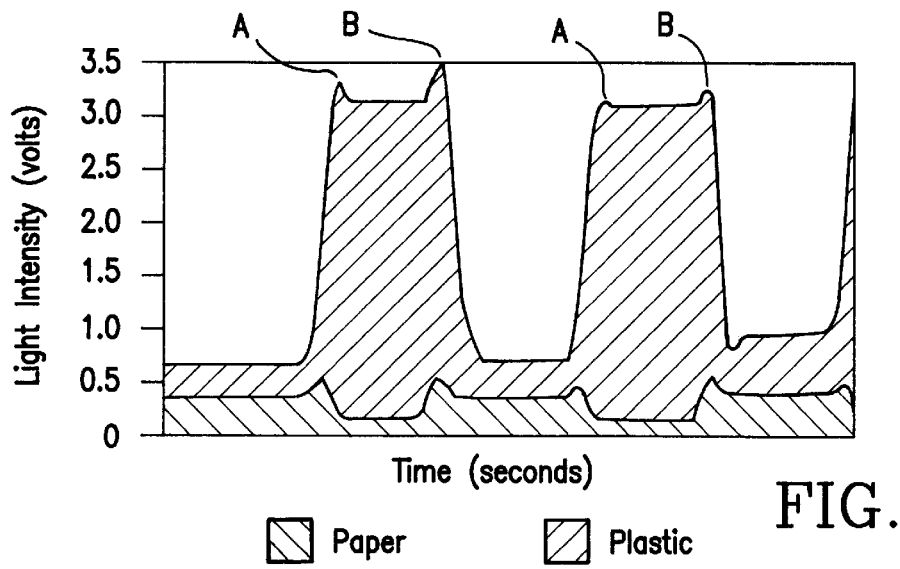
FIG. 3
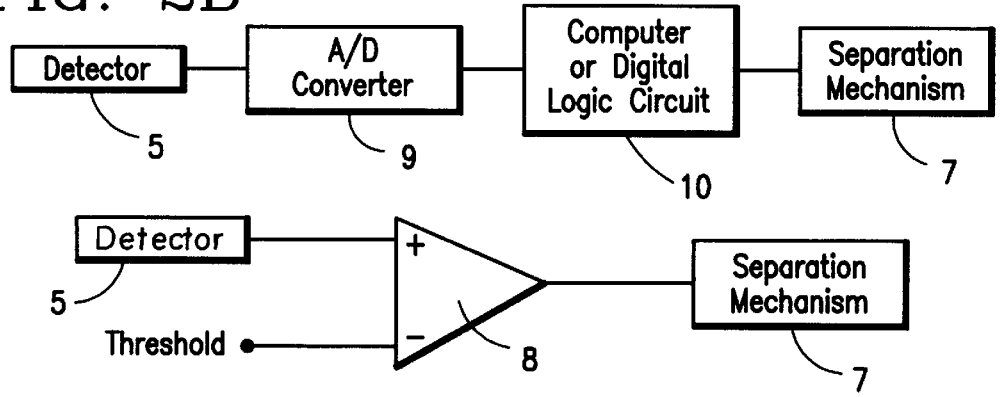
FIG. 2B
FIG. 2A
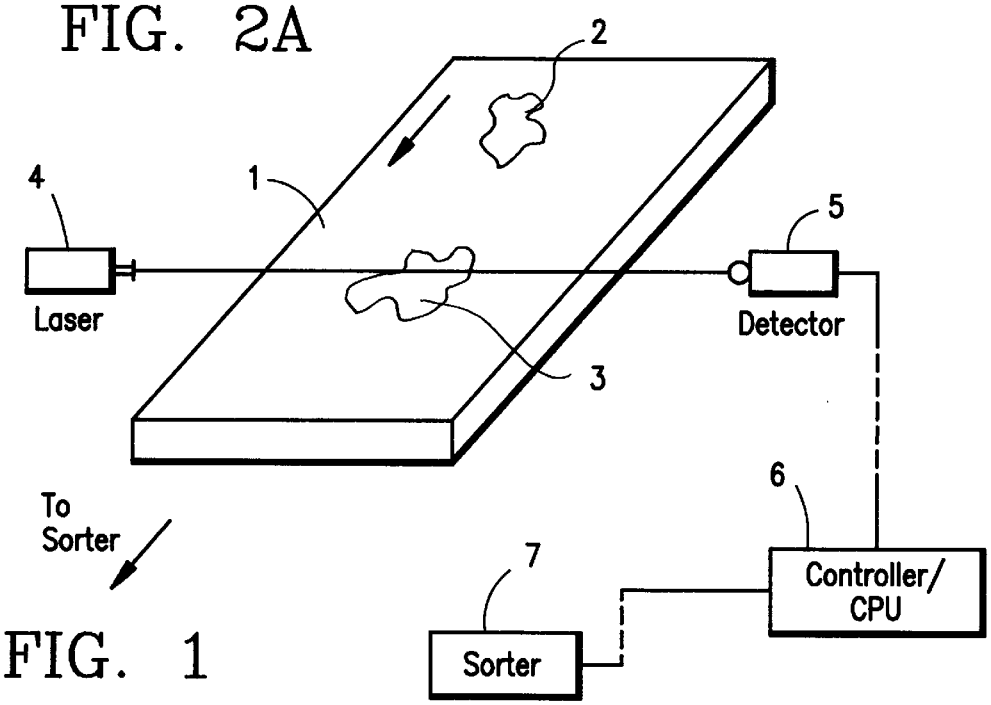
FIG. 1

APPARATUS AND METHOD FOR DISTINGUISHING PAPER ARTICLES FROM PLASTIC ARTICLES

BACKGROUND OF THE INVENTION

1. Field of the Invention

This invention relates to sorting of waste materials for recycling, and in particular to a method and apparatus for distinguishing paper objects from plastic objects in order to separate the paper objects from the plastic objects.

In particular, the invention relates to apparatus for distinguishing paper from plastic objects by using a conveyor, a laser and detector placed on opposite sides of the conveyor so that light is transmitted through the objects to be distinguished, and a thresholding circuit or software for distinguishing paper objects from plastics based on whether the transmitted light is above or below the threshold.

While it is well-known to analyze different types of objects based on the properties of light transmitted through the objects, it was not previously appreciated that paper and plastic articles could be distinguished in this manner. The invention is made possible by the discovery of the Inventor that paper and plastic objects have non-overlapping transmissivities with respect to coherent light when positioned a sufficient distance away from the detector, allowing paper and plastic objects to be distinguished through the use of a single light source and detector, and analysis by thresholding. The discovery was made by the Inventor, age 14, as part of a science fair project.

2. Description of Related Art (a) Introduction

The prior or related art includes numerous systems and methods for distinguishing glass from plastic and different types of plastics from each other using light transmission, but none for distinguishing paper from plastic, and none are currently in use in recycling plants or sorting facilities.

In order to distinguish plastic or glass objects from each other, complex spectral analyses and/or the use of electromagnetic wavelengths outside the visible spectrum are required. The resulting apparatus and methods are too complex or expensive to implement in a typical recycling plant or waste sorting facility. In contrast, the present invention is designed to be implemented with a minimum of equipment, and used in a typical sorting or recycling facility of the type that currently uses manual labor to separate paper from plastic articles.

Even though sorting by analysis of transmission or reflection spectra are known for the purpose of separating different plastics from each other, for separating glass from plastic, or for sorting such objects as fruit, the only currently available methods of separating paper articles from plastic articles are to separate the articles by hand, by using jets of air, or by elutriation. Generally, sorting and recycling of paper and plastic articles is a low margin activity, and the complex setups required of prior optical sorting arrangements have made them unattractive even for investigation with respect to sorting of paper and plastic articles.

The societal benefits of recycling paper, plastic, and other types of solid waste are of course obvious and, in most municipalities, special trucks regularly pick up recyclable waste and cart it to transfer stations or directly to recycling facilitates, which lessens the load at incinerators and landfills. In order to recycle the received materials, however, the materials must initially be separated into plastic, glass, metal, and paper. Glass and metal objects can easily and economically be separated from the waste stream by air classification or magnets, but the weight and other properties or plastic and paper articles make them more difficult to distinguish for purposes of separation.

In plants or facilities where air classification or elutriation is used, a significant amount of paper is missed and must be removed either through float/sink tanks or hydroclones. As a result, most organizations that collect waste for recycling still sort paper and plastic by hand.

The present invention uses a very simple arrangement involving an inexpensive monochromatic source laser and a detector that measures the intensity of light passing through the objects. The arrangement is sufficiently simple and effective that it is believed that a number of waste facilities would have adopted the method and apparatus if known, rather than rely on hand sorting or relatively inefficient air classification or elutriation. However, it has only become apparent that such a sorting method would work based on the results of the Inventor's investigations, which are described below in connection with FIG. 3. Basically, the invention is made possible by the discovery that paper and plastic have non-overlapping transmissivity spectra when the objects are placed between a laser source and a detector, at a minimum distance from the detector that can readily be determined. The Inventor is not aware of any reason why the spectra should not overlap, but the results summarized in FIG. 3 show that they do not.

(b) Discussion of Specific References

Many of the references directed to sorting of objects by analysis of transmitted light are directed to separation of materials such as different types of plastics that have more subtle differences in physical properties than is the case with paper and plastic, and that require complex measuring and analysis methods not suitable or economical for use in separating paper from plastic. For example, U.S. Pat. No. 5,141,110 discloses a system that measures the intensity of light passing through different types of plastics such as PET and PVC or vinyl using polarization filters in order to measure birefringence or polarizing properties of the materials. This method requires polychromatic light sources, polarizing filters, and relatively sensitive detectors, and is only suitable for separating very specific types of plastics having different crystalline structures.

U.S. Pat. Nos. 5,435,445 and 5,465,822, on the other hand, disclose apparatus for sorting a variety of different articles by various methods, including analysis of the intensity of light reflected from an object through a polarizing filter. However, the use of light intensity analysis in the systems described in these patents is reserved for discriminating PET from vinyl, discrimination of other types of objects being carried out by color and self-induction analysis.

Another system for differentiating different types of plastic articles, as opposed to paper and plastic articles, using light intensity analysis, is disclosed in U.S. Pat. No. 5,518,124. The system described in this patent appears to be suitable for use with a single wavelength of electromagnetic radiation, but requires very high frequency radiation such as x-rays, microwaves, or gamma rays. X-ray and other high frequency radiation sources are not only more expensive than lasers in the visible or near visible wavelengths, but are also significantly more hazardous and therefore require expensive safety measures. In addition, at the wavelengths described in this patent, the problem of irregular object shapes becomes significant and must be taken into account. In fact, this patent explicitly states in col. 7 lines 53–55 that a "problem arises if only a threshold comparator (such as disclosed in Giovanni, [which involves a radiation chamber into which items are individually fed and removed] is used in an attempt to distinguish between the polyester and PVC containers," namely the thickness of the containers. According to this patent, thresholding cannot be used to distinguish the types of articles with which the patent is concerned.

U.S. Pat. No. 5,405,014 discloses analysis of the intensities of light passing through beverage bottles to determine the type of bottle and identify any residues in the bottles. In order to perform such a broad spectrum analysis, however, it is again necessary to use polychromatic light, and in particular to determine the attenuation of a broad spectrum of wavelengths. The use of a spectrometer, as opposed to a simpler monochromatic light detector, greatly increase the cost and complexity of the system.

U.S. Pat. No. 3,747,755 discloses a device that is capable of separating paper from plastic but requires analysis of specular reflections from objects passing the detector, and in particular attenuation of different infrared wavelengths. In the 26 years since issuance of this patent, the system does not seen to have been put into practice, at least with respect to separation of paper from plastic, although the principle of utilizing infrared reflectivity is also mentioned in a later patent, U.S. Pat. No. 5,590,791, in combination with color sensing.

U.S. Pat. No. 3,980,180 discloses a transmissive article sorting device which involves separation of glass particles by transmissivity, and in particular colored particles. The apparatus disclosed in this patent is similar to that utilized by the present invention, but the patent does not anywhere suggest a potential application to separation of paper and plastic articles which, unlike the differently colored glasses or ceramics in the patent, do not necessarily have transmission properties suitable for use in distinguishing the objects, particularly when utilizing the light source described in the patent, which is an LED rather than a laser. The use of an LED light source limits the apparatus described in the patent to separation of objects that are transparent or translucent in ordinary visible light.

Other references that might be of interest from the standpoint of background are U.S. Pat. Nos. 3,781,531 and 3,216,568, directed respectively to detection of flaws in a material by analysis of reflected laser light, and sorting of objects by detecting a chemiluminescence or phosphorescence effect.

The prior art thus includes systems that use polarization of polychromatic light to separate different types of plastics with otherwise similar transmissivities, attenuation spectra for wide ranges of different materials to be separated, high frequency x-rays or gamma ray sources, and infrared reflectivity. The one patent disclosing separation of paper uses infrared reflectivity, while another patent that discloses analysis of radiation absorption by different objects specifically teaches away from thresholding, at least when applied to different types of plastic.

The present invention, in contrast, has the following unique combination of features:

a monochromatic light source and single detector;

thresholding;

application to sorting of paper and plastic articles or objects.

SUMMARY OF THE INVENTION

It is accordingly an objective of the invention to provide a practical method and apparatus for distinguishing paper from plastic objects or articles, which can be implemented using a single monochromatic visible light source and a single detector (although multiple light sources and detectors are not necessary outside the scope of the invention), and in which analysis may be carried out by simple thresholding rather than spectrum or polarization analysis.

The objective of the invention is achieved, in accordance with the principles of the preferred embodiment of the invention, by providing a coherent light source such as a laser, a device for conveying paper and plastic objects through the path of the laser, and a detector arranged to detect light passing through the objects and to measure the intensity of the light, connected to an analog thresholding circuit, computer, or digital logic circuit that determines whether a passing object is a paper object or a plastic object based on whether the measured light intensity is below or above a threshold. According to the principles of the invention, the objects passing between the light source and the detector must be a minimum distance from the detector that is determined by the points at which the intensity of light transmitted through a paper object decreases and the intensity of light transmitted through a plastic object increases.

It is the characteristic of paper and plastic objects that the transmission of light increases for plastic and decreases for paper that makes practical the apparatus and method of the invention. This characteristic was, as indicated above, first discovered by the Inventor, a summary of the results of the experiment that led to the discovery being included below.

BRIEF DESCRIPTION OF THE DRAWINGS

FIG. 1 is a schematic diagram showing the principal elements of an apparatus constructed in accordance with the principles of a preferred embodiment of the invention.

FIG. 2A is a schematic diagram of an analog thresholding circuit for use in connection with the apparatus of FIG. 1.

FIG. 2B is a schematic diagram of a digital thresholding arrangement which may be used with the apparatus of FIG. 1.

FIG. 3 is a graph of the intensities of transmitted light for paper and plastic articles in relation to time as the articles are moved towards and away from a detector arranged in the manner illustrated in FIG. 1.

DETAILED DESCRIPTION OF THE PREFERRED EMBODIMENTS

Figure 4:
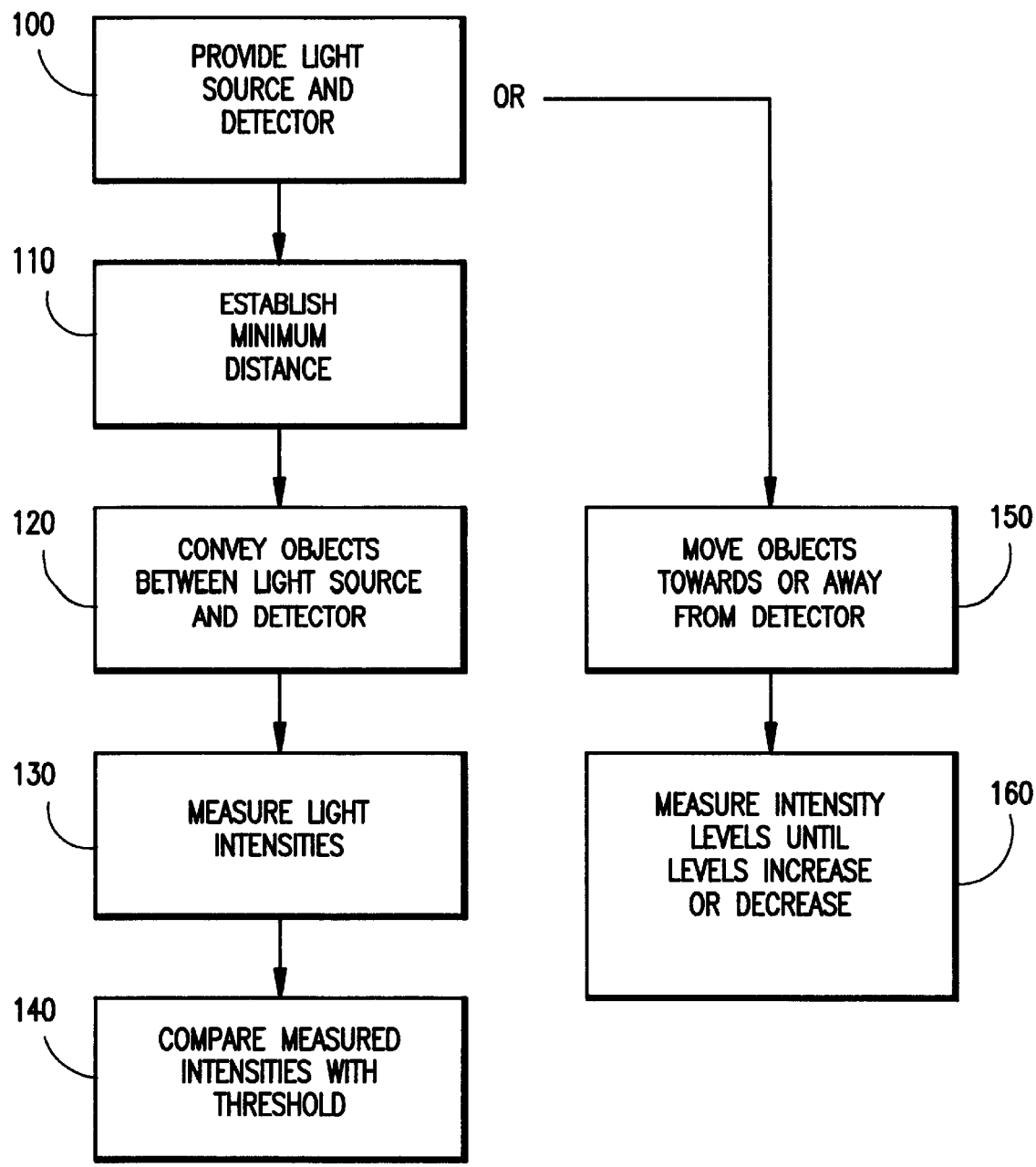
FIG. 4 is a flowchart illustrating a method of distinguishing paper from plastic articles according to the principles of the preferred embodiment of the invention.

As illustrated in FIG. 1, the present invention can be implemented by using a conveyor belt 1 to convey paper and plastic objects 2 and 3 past an identification device made up of a laser 4 and detector 5 positioned on opposite sides of the conveyor belt in such a manner that light from the laser passes through objects on the belt and is incident on the detector, the detector 5 being connected to a controller 6 that determines whether light incident on the detector is above or below a predetermined threshold. A mechanism 7 may be included to automatically separate out either paper or plastic objects based on the results of the threshold determination.

Those skilled in the art will appreciate that the conveyor belt 1 may be replaced by any device capable of carrying an object between the laser 5 and the detector 6, and that the laser and detector may be placed at any convenient orientation with respect to the conveyor, including vertical orientations in which the laser light shines through the conveyor.

Those skilled in the art will also appreciate that a variety of different lasers may be used as the laser 4, and that the type of detector 5 will depend on the type of laser chosen, so long as the detector is capable of measuring an intensity of light transmitted by a passing paper or plastic article. One example of a suitable laser is the commercially available helium neon gas laser. In addition, monochromatic coherent light sources other than lasers may be substituted for the illustrated laser.

Controller 6 may be implemented by a device as simple as the analog comparator 8 illustrated in FIG. 2A, or by an A/D circuit 9 and digital computer or logic circuit 10, as illustrated in FIG. 2B. As indicated above, what is not needed is a broad spectrum analyzer or spectrometer, polarizing filters, or color filters, except as necessary to eliminate background light. Whether in the form of an analog circuit or a digital computer, the controller compares the intensity of light measured by detector 5 with a threshold and outputs a signal indicative of whether the measure intensity is above or below the threshold.

While the invention is implemented by simple thresholding, it is noted that additional processing circuitry is nevertheless within the scope of the invention. In particular, filtering circuits for filtering out noise or the effects of reflections, and circuits that determine whether an object is passing may be included. Also, additional circuitry or software could be included to make finer distinctions once a determination has been made as to whether the object is paper or plastic based on where the intensity falls within the non-overlapping paper or plastic spectra.

In the case of a simple comparator, the thresholding could be carried out by outputting a signal whenever the intensity detected by the detector drops below a threshold indicative of the presence of a paper object, eliminating the need to determine whether an object is passing since the intensity detected by the detector when no object was present would be above the threshold.

Alternatively, rather than a single threshold, the invention could be implemented by using dual thresholds, one of which is a maximum intensity below which an object is determined to be paper and the other of which is a minimum intensity above which an object is determined to be plastic. This would enable exceptional objects that fall between the normal intensity spectra, such as non-paper and non-plastic objects unintentionally included in the waste stream, mixed material objects, and other objects that do not have the expected transmissivities to be flagged and removed by hand.

The output of the controller is, in the preferred embodiment of the invention, supplied to a sorting mechanism such as a gate, blower, or the like, that removes either paper or plastic articles, or both, from the conveyor and sends to appropriate destinations based on the output of the detector. The particular mechanism used to accomplish the actual sorting of the paper and plastics articles after they have been distinguished forms no part of the present invention.

As indicated above, the invention is based on the discovery that the transmissivity of plastic increases when the plastic is a predetermined distance from the detector, and the transmissivity of paper decreases when the paper is moved away from the detector. This is graphically illustrated in FIG. 3, which shows the results of a test in which a paper object is moved towards and away from the detector. At points A the object is moved beyond the threshold distance and at point B the object is moved closer than the threshold distance. It can be seen that the voltage levels recorded by the detector is approximately flat within the threshold distance and approximately flat beyond the threshold distance, but that there is a dramatic increase or decrease at the threshold. As a result of this effect, it can be seen that so long as the object is beyond the distance corresponding to points A, paper and plastic can easily be distinguished, but if the object is closer than point A, the paper and plastic are virtually indistinguishable.

In the test setup, which used a helium neon gas laser and a light probe connected to a computer by a Universal Lab Interface, with all intensity readings being transferred to a computer generated graph, the range of light intensities for plastic was from 2.92 to 1.96 volts, and the range for paper was from 0.91 to 0.52 volts. A second test setup with two sets of lasers and light probes connected to the same Universal Lab Interface, the sets of lasers and light probes facing in opposite directions, did not reveal a marked difference in the graphs for paper and plastic.

The threshold or thresholds for the set-up illustrated in FIG. 3 could therefore be anywhere from approximately 0.91 volts to 2.96 volts, with intensities below 0.91 volts being clearly indicative of paper and intensities above 2.96 volts being indicative of plastic, so long as the detector were positioned at distances from the detector corresponding to the portion of the graph shown in FIG. 3 that lies between points A and B.

The graph shown in FIG. 3 gives the results in terms of time because the test setup was incapable of recording the distance. However, those skilled in the art will appreciate in practice that a correlation can easily be made between the time axis of the graph of FIG. 3 and the distance of the object from the detector, and in particular the distance corresponding to points A at which the intensity level changes. Those skilled in the art will further appreciate that the distance corresponding to points A could also be measured from the laser rather than the detector with equivalent results since the laser and detector are a fixed distance apart.

As illustrated in FIG. 4, the method of practicing the invention involves providing a coherent light source and a detector that is a fixed distance from the light source (step 100), and establishing a distance from the objects at which paper and plastic objects are easily distinguished by their light intensities (step 110), for example by moving objects away from or towards the detector at least once until the light intensity increases, in the case of plastic, or decreases, in the case of paper. Paper and plastic objects may then be conveyed so that they pass between the light source and the detector (step 120), the resulting light intensities measured (step 130), and a determination made as to whether the objects are paper or plastic by, for example, comparing the measured intensities with a threshold (step 140).

Alternatively, as illustrated in FIG. 4, it is also within the scope of the invention to distinguish paper from plastic articles based on the shape of the intensity curve, and in particular the marked increase and decrease in light intensity, that occurs when a paper or plastic article is moved towards or away from the detector, rather than based on the absolute value of the light intensity as the article is moved passed the detector. This may be accomplished, as illustrated in FIG. 4, by moving the paper or plastic object towards or away from the detector rather than past the detector (step 150) and measuring intensity levels until the intensity level either increases or decreases (step 160), the direction of change indicating whether the object is paper or plastic. In addition, the latter method could be used to also identify objects in which the intensity level does not change with distance, such as glass objects, allowing them to also be separated from the waste stream.

Those skilled in the art will appreciate that the latter method of distinguishing paper from plastic articles or objects can be carried out by using a controller made up of any combination of elements from a simple differentiator for determining the slope of the intensity levels, the differentiator connected to a thresholding device such as the one shown in FIG. 2A, to an arrangement in which analysis is carried out solely by digital computer software.

Having thus described a preferred embodiment of the invention with sufficient particularity to enable those skilled in the art to easily make and use the invention, and having described several possible variations and modifications of the preferred embodiment, it should nevertheless be appreciated that still further variations and modifications of the invention are possible, and that all such variations and modifications should be considered to be within the scope of the invention. Accordingly, the scope of the invention should not be limited by the above description, but rather should be interpreted solely in accordance with the appended claims.

I claim:

1. Apparatus for distinguishing paper from plastic objects, comprising:

a coherent light source;

a detector arranged to measure an intensity of light that reaches the detector from said light source, wherein when a plastic object and a paper object are respectively positioned between the light source and the detector at a first distance from the detector, the intensities of light measured by the detector for the plastic object and the paper object are approximately equal, wherein when the plastic object is positioned between the light source and the detector at a second distance that is farther from the detector than the first distance, the intensity of light measured by the detector for the plastic object is substantially greater than the intensity of light measured by the detector for the plastic object when the plastic object was at the first distance;

wherein when the paper object is positioned between the light source and the detector at a second distance that is farther from the detector than the first distance, the intensity of light measured by the detector for the paper object is substantially less than the intensity of light measured for the paper object when the paper object was at the first distance, and wherein said second distance is selected as a minimum distance from said detector;

a device arranged to convey said objects past the detector such that when said objects are between the detector and the light source, said objects are at least said minimum distance from the detector; and a thresholding device connected to said detector for comparing the light intensity measured as the object is moved between the detector and the light source with at least one threshold intensity, said threshold intensity being an intensity either below which the object is determined to be paper or above which the object is determined to be plastic.

2. Apparatus as claimed in claim 1, wherein said conveying device is a conveyor belt.

3. Apparatus as claimed in claim 1, wherein said coherent light source is a helium neon gas laser.

4. Apparatus as claimed in claim 1, wherein said thresholding device includes a comparator circuit.

5. Apparatus as claimed in claim 1, wherein said thresholding device includes an analog-to-digital converter and a digital computer.

6. Apparatus as claimed in claim 1, wherein said thresholding device outputs a signal indicative of whether said object is a paper or a plastic object, and further comprising means for separating said paper object from said plastic object based on said signal output by the thresholding device.

7. A method of distinguishing paper objects from plastic objects, comprising the steps of:

(a) providing a coherent light source and a detector a fixed distance away from the coherent light source;

wherein when a plastic object and a paper object are respectively positioned between the light source and the detector at a first distance from the detector, the intensities of light measured by the detector for the plastic object and the paper object are approximately equal, and wherein when the plastic object is positioned between the light source and the detector at a second distance that is farther from the detector than the first distance, the intensity of light measured by the detector for the plastic object is substantially greater than the intensity of light measured by the detector for the plastic object when the plastic object was at the first distance; and wherein when the paper object is positioned between the light source and the detector at a second distance that is farther from the detector than the first distance, the intensity of light measured by the detector for the paper object is substantially less than the intensity of light measured for the paper object when the paper object was at the first distance;

(b) selecting said second distance as a minimum distance from the detector and, based on said measurements of light intensities measured by said detector at said minimum distance from the detector, establishing at least one threshold intensity, wherein when the intensity of light passing through an object and measured by said detector is below the threshold intensity, the object is determined to be a paper object, and wherein when the intensity of light passing through the object and measured by the detector is above the threshold intensity, the object is determined to be a plastic object;

(c) passing paper and plastic objects between the coherent light source and the detector at a distance greater than said minimum distance from said second distance, and measuring intensities of light passing through the objects;

(d) comparing the light intensities measured as the paper and plastic objects are moved between the detector and the light source with said threshold intensity.

8. A method as claimed in claim 7, wherein step b comprises the steps of moving a paper object along a line extending between the detector and light source; measuring an intensity of light incident on the detector as the paper object is moved along said line; moving a plastic object along said line and measuring amount of light incident on the detector, selecting a point at which the intensity of light incident on the detector increases for a plastic object and decreases for a paper object as said minimum distance, said intensity of light being represented by a voltage level, and choosing to represent said threshold intensity a voltage level between the voltage levels recorded for said paper and plastic objects when said paper and plastic objects are beyond said minimum distance from said detector.

9. A method as claimed in claim 8, further comprising the step of separating paper objects from plastic objects based on a signal output by said detector.

* * * * *